(12) United States Patent
Ngai et al.

(10) Patent No.: US 6,982,143 B1
(45) Date of Patent: Jan. 3, 2006

(54) NORMALIZING AND AMPLIFYING RNA

(75) Inventors: John Ngai, Berkeley, CA (US); David Lin, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1059 days.

(21) Appl. No.: 09/597,608

(22) Filed: Jun. 20, 2000

(51) Int. Cl.
*C12Q 1/68* (2006.01)
*C12Q 1/48* (2006.01)
*C12P 19/34* (2006.01)
*C07H 21/04* (2006.01)

(52) U.S. Cl. .......................... 435/6; 435/15; 435/91.1; 435/91.2; 435/91.21; 435/91.5; 536/24.33

(58) Field of Classification Search .................. 435/5, 435/6, 15, 91.1, 91.2, 91.21, 91.5, 91.51; 935/78; 536/24.33
See application file for complete search history.

(56) References Cited

U.S. PATENT DOCUMENTS

| | | | | |
|---|---|---|---|---|
| 5,514,545 A | * | 5/1996 | Eberwine | 435/6 |
| 5,591,575 A | * | 1/1997 | Hampson et al. | 435/6 |
| 5,866,327 A | * | 2/1999 | Gudkov et al. | 435/6 |
| 6,114,152 A | * | 9/2000 | Serafini et al. | 435/91.2 |

OTHER PUBLICATIONS

Stratagene Catalog, 1995, p. 109.*

* cited by examiner

*Primary Examiner*—W. Gary Jones
(74) *Attorney, Agent, or Firm*—Richard Aron Osman

(57) ABSTRACT

The invention provides methods and compositions for normalizing and amplifying RNA populations. The methods generally comprise the steps of copying message RNA (mRNA) to form first single-stranded (ss) cDNA; converting the first ss-cDNA to first double-stranded (ds) cDNA; linearly amplifying the first ds-cDNA to form first amplified RNA (aRNA); tagging the 3' end of the first aRNA with a known sequence to form 3'-tagged first aRNA; copying the 3'-tagged first aRNA to form second ss-cDNA; and normalizing the mRNA and/or the first aRNA.

19 Claims, 6 Drawing Sheets

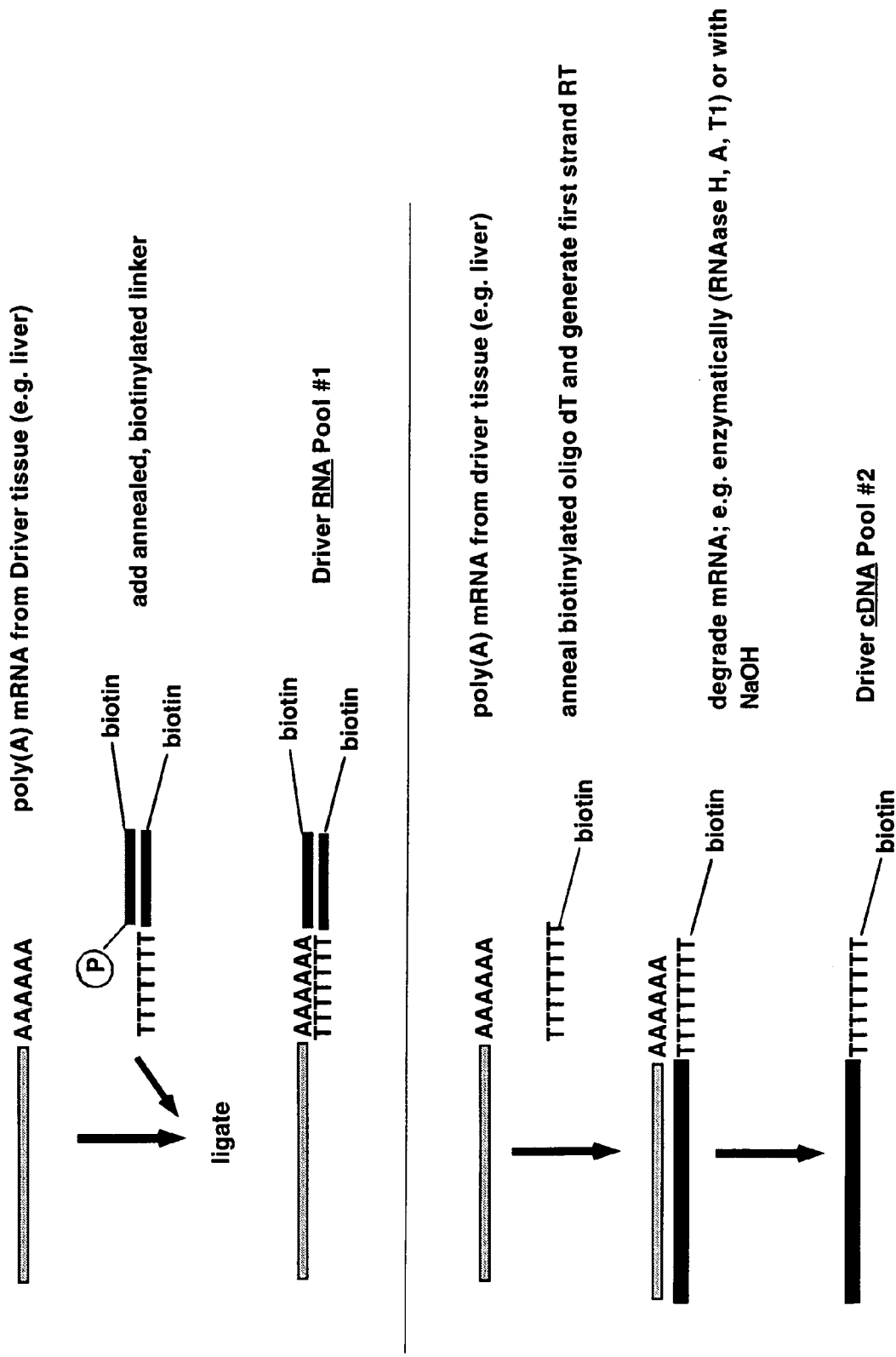

```
SEQUENCE LISTING

<160> NUMBER OF SEQ ID NOS:  5

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 1
taatacgact cactataggg aga                                              23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 2
taatacgact cactataggc gc                                               22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
taatacgact cactataggg cga                                              23

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 4
cgttgatgtg acccttctac ttgtatat                                         28

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 5
caagtataac ggtcacatca acgttttttt tttttttttt tttt                       44
```

NORMALIZING AND AMPLIFYING RNA

The disclosed inventions were made with Government support under Grant (Contract) Nos. 1R01 MH61665 and 2RO1DC02253 awarded by the National Institutes of Health. The government may have rights in these inventions.

INTRODUCTION

Field of the Invention

The field of this invention is normalizing and linearly amplifying polynucleotides.

BACKGROUND

The ability to characterize cells by gene expression provides a wide variety of applications in therapy, diagnostics and bio/medical technology. However, in many of these applications, the starting or source material such as stem cells, cancerous cells, identified neurons, embryonic cells, etc. is highly limiting, making it necessary to amplify the targeted mRNA populations. Two existing methods for amplifying mRNA populations suffer from significant limitations. One method, the Brady and Iscove method (Brady et al., 1990, Methods Mol & Cell Biol 2, 17–25), produces only short (200–300 bp), extreme 3' fragments of mRNAs using a PCR-based method which exponentially amplifies artifacts. A second method, the Eberwine protocol (Eberwine et al. (1992) Proc. Natl. Acad. Sci USA 89, 3010–3014) provides sequential linear amplification steps and is the current method of choice for amplifying mRNA populations from limiting material. Nevertheless, this protocol suffers from a number of deficiencies. For example, the amplified product does not represent full-length aRNA for many endogenous mRNAs, and hence the method is of limited use for generating probes or cDNA libraries.

There are two commonly used methods to analyze labeled mRNA populations. The first is to use microarray technology, in which PCR products are spotted at high density on microscope slides. This technology has an estimated sensitivity of 10 copies per cell. At this level, it would be barely possible to detect rare transcripts, if at all. This is due, in part, to the fact that rare transcripts will incorporate less fluorescent label than highly expressed transcripts, and will not be as bright. This same principle applies to the use of filter technology, in which cDNAs or PCR products are spotted onto a nylon membrane. This technology has an estimated sensitivity of ~50 copies/cell and would clearly not detect any rare transcripts.

Normalization allows the detection of RNA transcripts expressed at low levels. This is important because ~30% of all transcripts are present at 1–10 copies per cell ("rare" transcripts). Other genes are expressed at much higher levels, for example from 50 (moderately low) to 10,000 (high) copies per cell and up. Thus, if a population of poly(A) mRNA is labeled using reverse transcriptase, oligo dT, and radioactive/fluorescent nucleotides, the great majority of label will be incorporated into highly expressed transcripts. Normalization generates a reduction in the number of highly expressed transcripts relative to more rare transcripts. In an ideal case, a perfect normalization yields a single copy of every unique transcript in a population. As a result, all transcripts are equally labeled, and can be easily detected by either microarray or by filter.

Normalization/subtraction removes highly expressed "tester" transcripts that are in common with a "driver" population. The remaining, unhybridized sample are then labeled and analyzed. A significant limitation is that the subtracted product is often present in very low amounts. This makes experiments technically very difficult. Moreover, often times a single round of normalization is insufficient to either normalize or subtract two populations. Thus, the small amount of product that remains from the first normalization/subtraction then has to be used in a second, and sometimes a third, round to more fully subtract a population. By this time, very little product remains in the tester population, making it difficult to label and analyze experimentally. In order to get around this problem, PCR has been employed to amplify the differences that remained following a round of normalization/subtraction. This increases the amount of unhybridized tester to a level such that additional rounds of subtraction can be performed. Currently, three to four rounds of subtraction and PCR amplification are required to fully subtract two populations and identify unique transcripts in either pool. One problem with PCR is that some transcripts are preferentially amplified over others. Thus, in amplifying the differences left after a subtraction round, some will not be amplified, while others will be amplified at higher levels than others. This exaggerates the need for another round of subtraction.

The present invention provides the benefits of normalization without the limitations of PCR by combining a normalization protocol with a linear amplification protocol. By using an RNA polymerase like T7 to amplify the differences following a subtraction instead of PCR, the differences are linearly amplified. In addition, such polymerases do not show the same bias in amplifying transcripts that PCR does. As a result, it is easier to assure that what remains following a round of amplification will not be additionally biased by the subsequent amplification.

Relevant Literature

Sippel (1973) Eur. J. Biochem. 37, 31–40 discloses the characterization of an ATP:RNA adenyl transferase from *E. coli* and Wittmann et al. (1997) Biochim. Biophys. Acta 1350, 293–305 disclose the characterization of a mammalian poly(A) polymerase. Gething et al. (1980) Nature 287, 301–306 disclose the use of an ATP:RNA adenyltransferase to polyadenylate the '3 termini of total influenza virus RNA. Eberwine et al. (1996) U.S. Pat. No. 5,514,545 describes a method for characterizing single cells based on RNA amplification. Eberwine et al. (1992) Proc. Natl. Acad. Sci USA 89, 3010–3014, describe the analysis of gene expression in single live neurons. Van Gelder, et al. (1990) Proc Natl Acad Sci U S A.87(5):1663–7. describe amplified RNA synthesized from limited quantities of heterogeneous cDNA. Gubler U and Hoffman B J. (1983) Gene (2-3), 263–9, describe a method for generating cDNA libraries, see also the more recent reviews, Gubler (1987) Methods in Enzymology, 152, 325–329 and Gubler (1987) Methods in Enzymology, 152, 330–335. Clontech (Palo Alto, Calif.) produces a "Capfinder" cloning kit that uses "GGG" primers against nascent cDNAs capped with by reverse transcriptase, Clontechniques 11, 2–3 (October 1996), see also Maleszka et al. (1997) Gene 202, 39–43.

Copending U.S. Ser. No. 09/049,806 now, U.S. Pat. No. 6,114,152 and U.S. Ser. No. 09/566,570 describe methods, such as using polyadenyltransferase to add known 3' sequences to aRNA molecules, which may be used in the subject methods.

SUMMARY OF THE INVENTION

The invention provides methods and compositions for normalizing and amplifying RNA populations. The methods generally comprise the steps of:
(a) copying mRNA to form first ss-cDNA;
(b) converting the first ss-cDNA to first ds-cDNA;
(c) linearly amplifying the first ds-cDNA to form first aRNA;
(d) tagging the 3' end of the first aRNA with a known sequence to form 3'-tagged first aRNA;
(e) copying the 3'-tagged first aRNA to form second ss-cDNA; and
(f) normalizing the mRNA and/or the first aRNA. Note that the normalizing step (f), may be implemented prior to step (a), prior to step (d), or prior to both.

The mRNA copying step comprises contacting the mRNA with a primer and an RNA polymerase promoter. The primer may be designed to hybridize with the polyA tail (e.g. comprising an oligo dT sequence) and/or with an internal mRNA sequence. Alternatively, where the starting material is amplified RNA, or aRNA, the known sequence may comprise a poly(T) sequence or the complement of a known internal mRNA sequence. Exemplary RNA polymerase promoters include promoters of T7, T3 and SP6. In a particular embodiment, the primer further comprises an affinity tag, such as biotin.

The converting step may be effected by contacting the first ss-cDNA with RNase H and a DNA polymerase under conditions whereby the RNase H nicks the associated mRNA and the DNA polymerase initiates conversion at a noncovalently joined heteroduplex region and copies the first ss-cDNA to the first ds-cDNA. The reaction conditions generally provide for nominal nicking of the RNA strand of the heteroduplexes by the RNase H, in which case a DNA polymerase having 5' exonuclease activity is used (e.g. DNA Pol I). Alternatively, higher RNAse concentrations may be used, effecting mRNA strand nicking sufficient to permit use of a polymerase without 5' exonuclease acivity (such as klenow).

The tagging step adds a known 3' sequence and may be effected by any convenient method. In one embodiment, the sequence is added by contacting the first aRNA with an oligonucleotide and a ligase, whereby the ligase adds the oligonucleotide to the 3' end of the first aRNA to form the 3'-tagged first aRNA. In another embodiment, the tagging step comprises contacting the first aRNA with a nucleotide (such as A, C or G) and a polyadenyltransferase under conditions whereby the polyadenyltransferase adds the nucleotide in series to the 3' end of the first aRNA to form the 3' tagged first aRNA.

The amplifying step may be effected with any convenient RNA polymerase compatible with the subject protocols; suitable examples include T7, T3 and SP6.

The normalization step generally comprises hybridizing the mRNA or the first aRNA with driver polynucleotides and then separating an unhybridized fraction of the mRNA or first aRNA. A wide variety of methods may be used to effect the separation, such as hydroxyapatite-based affinity separation and biotin-streptavidin-based affinity separation.

Applications of the method may comprise further steps, for example, iteratively repeating the copying-amplifying-normalizing (or normalizing-copying-amplifying) steps to effect increasing levels of substractive hybridization. Hence, in particular embodiments, the method further comprises the steps of: converting the second ss-cDNA to second ds-cDNA and linearly amplifying the second ds-cDNA to form second aRNA. This second aRNA may be further normalized, and optionally, the method may be continued by copying the second aRNA to form third ss-cDNA; converting the third ss-cDNA to third ds-cDNA; and linearly amplifying the third ds-cDNA to form third aRNA. The various protocol steps may be variously repeated and/or recombined in alternative permutations depending on the starting material, desired level of subtraction, nature of driver material, etc.

The invention also provides kits for practicing the subject methods and protocols. These generally comprise one or more reagents used in the methods and instructions describing protocols embodying the subject methods. In a particular embodiment, the kits include premeasured portions of oligo dT T7 biotinylated primer, T7 RNA polymerase, annealed biotinylated primers (used to make Driver pool #1, see FIG. 3), streptavidin beads, polyadenyl transferase, reverse transcriptase, RNase H, DNA pol I, buffers and nucleotides.

BRIEF DESCRIPTION OF THE FIGURES

FIG. 3 is a schematic showing generation of driver pools #1 and #2 as used in the protocols outlined in FIGS. 1A–1B and in FIGS. 2A–2C.

DETAILED DESCRIPTION OF PREFERRED EMBODIMENTS OF THE INVENTION

Figure 1A:
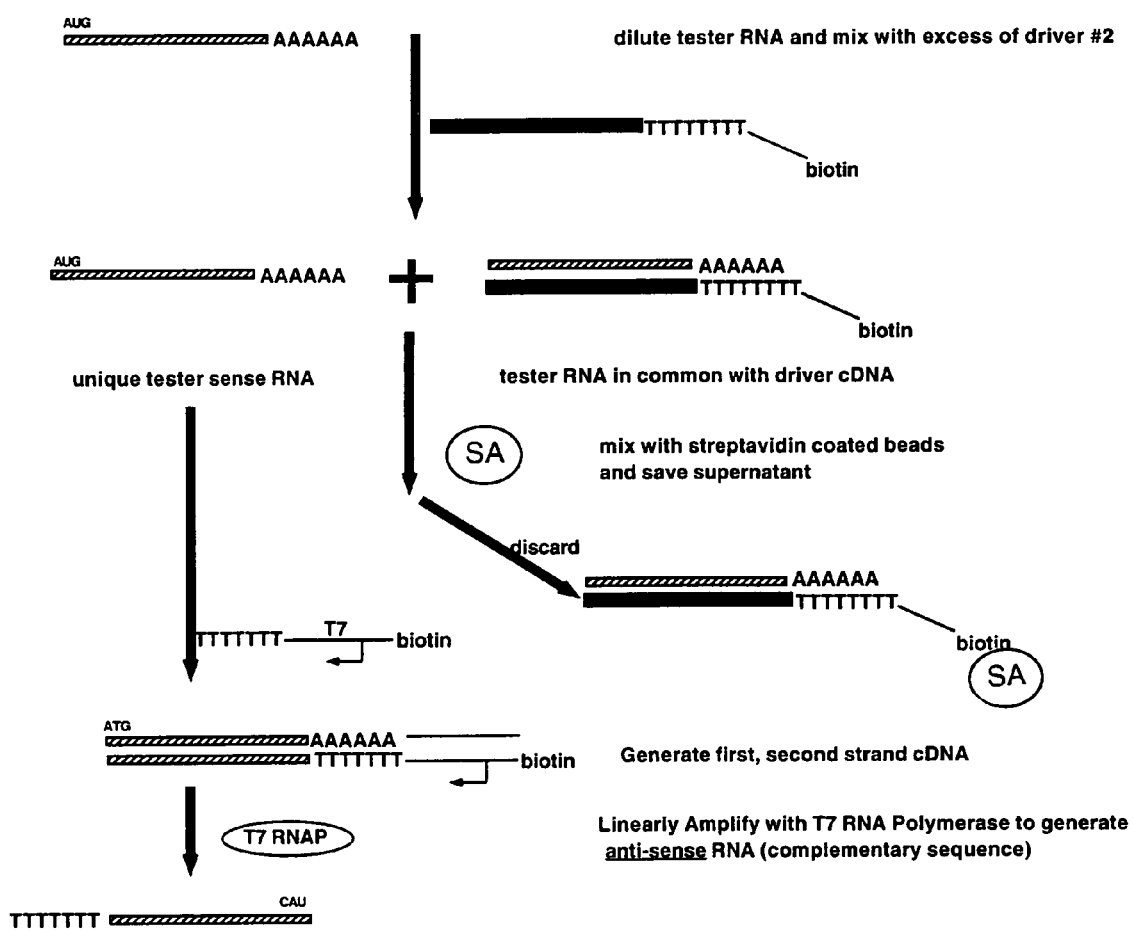
FIGS. 1A–1B is a schematic of one embodiment of the invention for normalizing unamplified RNA pools.
Figure 1B:
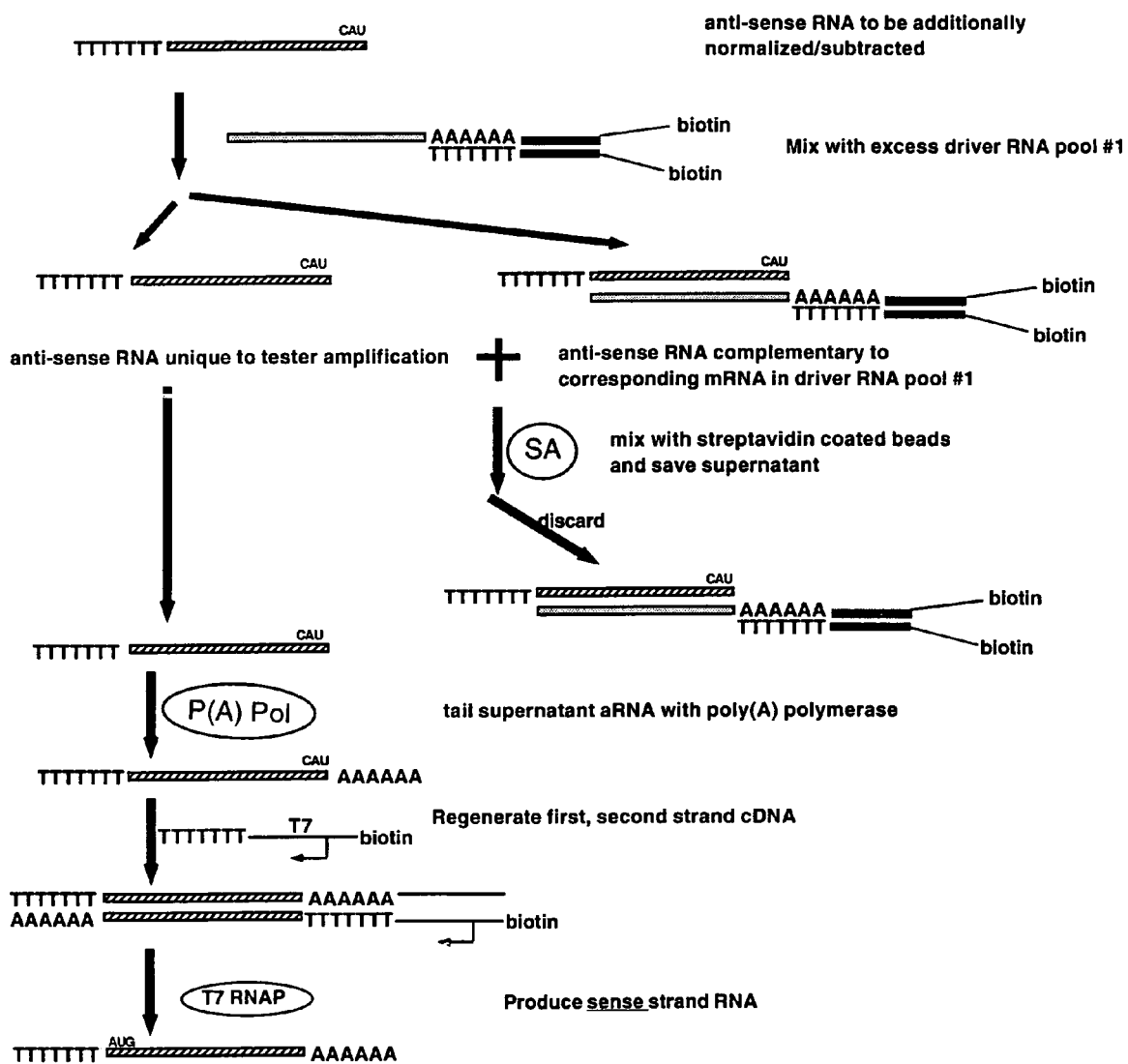
Figure 2A:
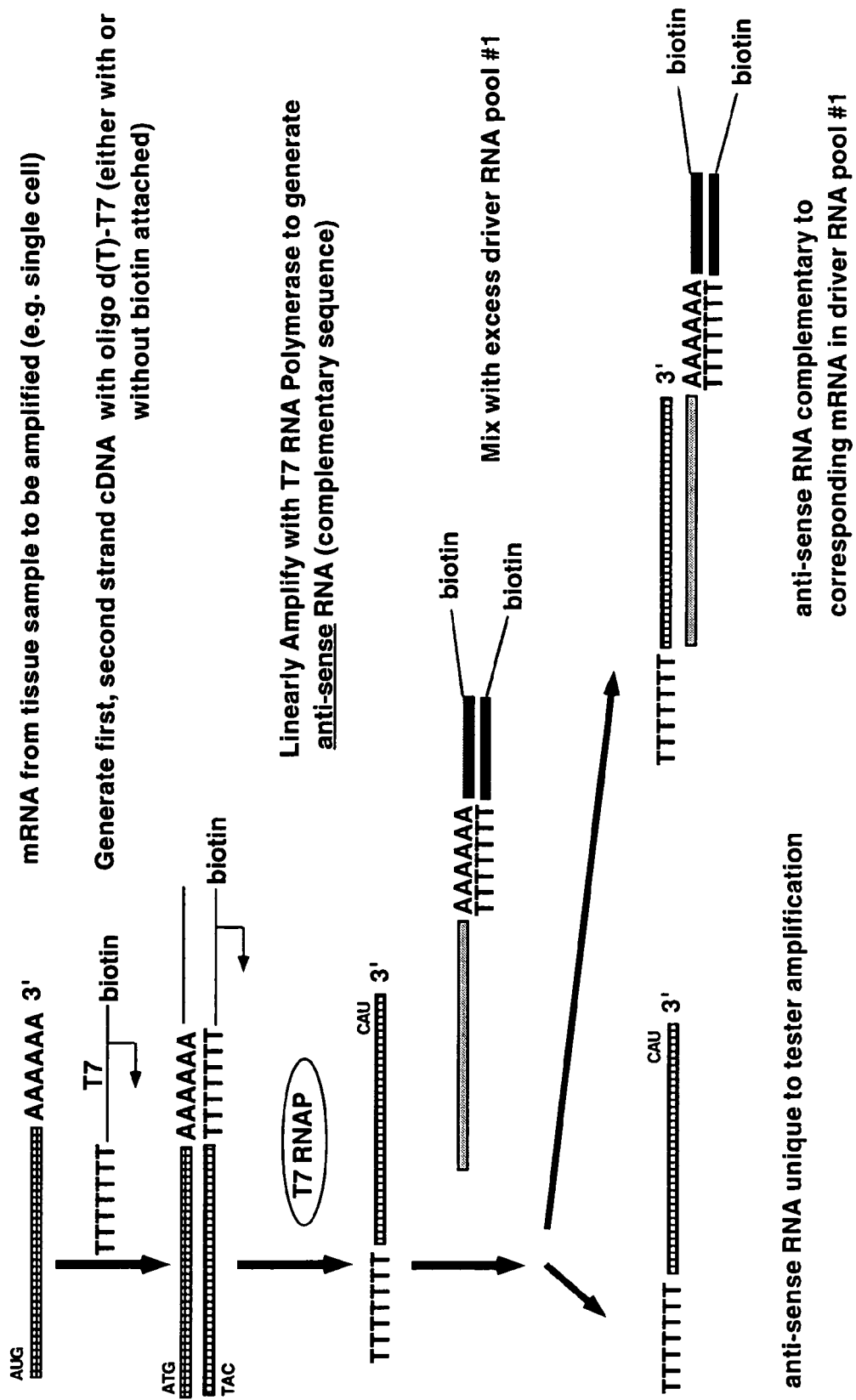
FIGS. 2A–2C is a schematic of another embodiment of the invention for normalizing/subtracting during amplification.
Figure 2B:
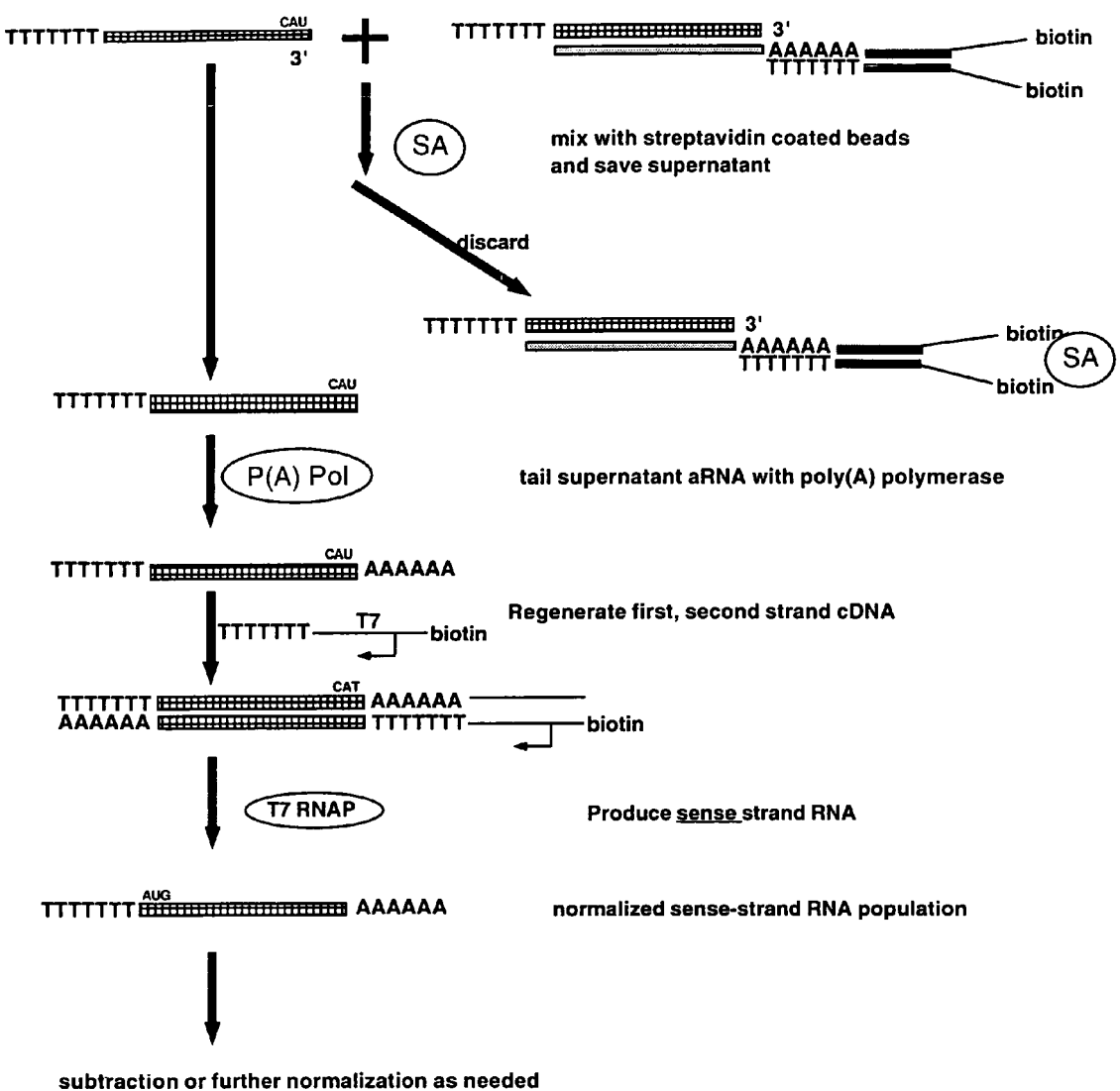
Figure 2C:
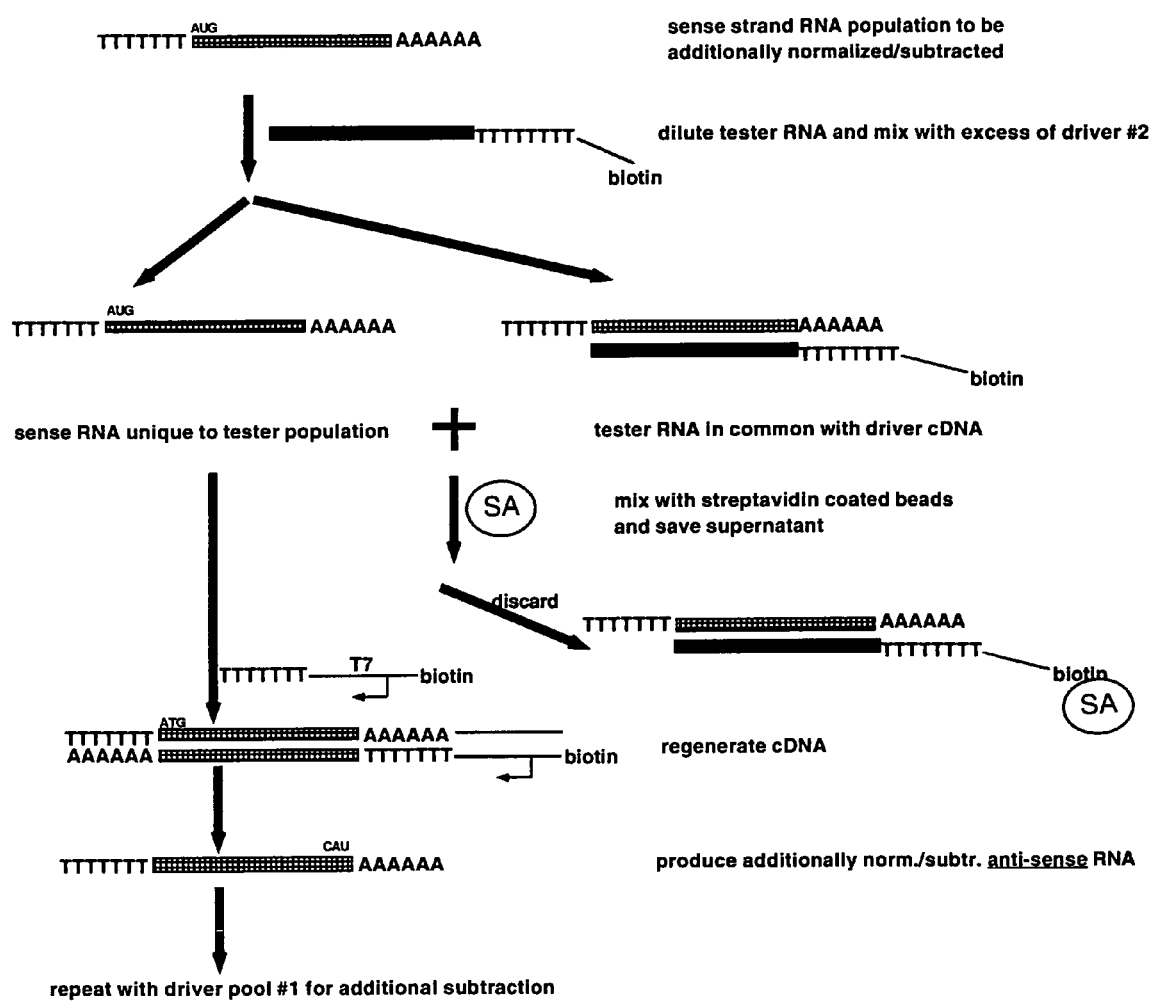

The following preferred embodiments and examples are offered by way of illustration and not by way of limitation.

The subject methods and kits provide a wide variety of applications where it is advantageous to normalize or normalize and subtract an RNA population. For example, in one application, we amplify mRNA from a single cell type, such as a particular neuron, and compare the entire population of mRNAs present in this single cell with that of another. In practice even after this amplification, a normalization is often necessary in order to detect rare transcripts. Thus, it is convenient to "normalize as you go", i.e. normalize/subtract during amplification; however, normalization can also be done following the amplification. Exemplary applications of the methods are diagramed in the accompanying Figures.

The starting material generally comprises a population of mRNA species having a diversity of abundances, whereby the method effects normalization, i.e. reduces the diversity of abundances by selectively removing molecules of higher abundance. Normalization generally requires separating the products which have not hybridized to a population of "driver" polynucleotides from the ones which have. A wide variety of separation techniques may be used, such as passing the normalized product over hydroxyapatite (HAP) columns. In this method, HAP binds to single stranded products, and double-stranded products flow through. The bound products are then eluted off. Alternatively, any convenient hapten affinity label-binding partner pair, such as biotin-avidin, digoxigenin-anti-digoxigenin, etc. can be used to separate subtracted polynucleotides. For example, biotinylated nucleotides can be incorporated into the driver RT cDNA, which can then be removed by streptavidin. Subtraction is effected by iteratively repeating the hybridization and separation steps. Note that normalization and/or subtraction can be implemented at one or more of several positions in the protocol, e.g. at the level of mRNA and/or one or more amplified RNA (aRNA) populations, which may be sense or anti-sense, alternating with the number of subtractive hybridization repeats.

Accordingly, the invention provides methods and compositions for making tagged driver RNA useful in the subject protocols. In a particular embodiment, the methods comprise the steps of: (a) combining linkers with a population of RNA species, wherein each linker comprises a first oligo comprising a first tagged annealing region and a second oligo comprising in 5'-3' direction a second tagged annealing region and a capture region, wherein the annealing regions are complementary and annealed to each other; and each RNA species comprises a target region complementary to the capture region, under conditions wherein the target regions hybridize to the capture regions; and (b) ligating the target regions to the first tagged annealing region to form tagged driver RNA.

The annealing regions may have any convenient complementary sequence of length sufficient to provide protocol-required hybridization dynamics, generally at least 20 nucleotides in length, and may be tagged in any convenient way such as with biotin, digoxigenin, an epitope tag, etc. Similarly, the driver may derive from any convenient RNA source material, though in a particular application the driver derives from mRNA or mRNA subsets of defined cell types. The capture region will with the target regions; for example, in the case of mRNA targets, the target region will generally be an internal conserved sequence or an polyA region. In the latter case, polydT provides a suitable capture region sequence, generally approximately 15 to 25 nucleotides in length.

In a particular example, the linkers are diagrammed in FIG. 3. The first linker sequence is the top strand that contains the phosphate and the biotin: 5' phosphate-CGT-TGATGTGACCCTTCTACTTGTATAT-biotin 3' (SEQ ID NO:4). The second oligo sequence is the bottom strand that contains oligo (dT), complementary sequence to top strand, and biotin: 5' biotin-CAAGTAGAAGGGTCACAT-CAACGTTTTTTTTTTTTTTTTTTTT 3' (SEQ ID NO:5). As shown in FIG. 3, the oligos are first annealed to one another to form a linker/adapter. The linker/adapter is then mixed with mRNA to anneal the oligo (dT) and poly(A) sequences, and then T4 DNA Ligase is added to join the mRNA to the linker/adapter, displacing the phosphate group.

The tagging step (which provides for recovery of more full-length normalized transcripts than can be obtained by priming with random hexamers) may be effected by any convenient method. For example, a polyadenyltransferase or poly(A) polymerase may be used to add selected nucleotides to the 3' end. Poly(A) polymerases may be derived from a wide variety of prokaryotic and eukaryotic sources, are commercially available and well-characterized. In another example, a ligase may be used to add one or more selected oligonucleotides. These enzymes are similarly readily and widely available from a wide variety of sources and are well characterized. The added known 3' sequence is sufficient to provide a target for a primer, otherwise the nature of the added known sequence is a matter of convenience, limited only by the addition method. For example, using ligase mediated oligonucleotide addition, essentially any known sequence that can be used as target for a primer may be added to the 3' end. With polyadenyltransferase mediated addition, it is generally more convenient to add a poly(N) sequence, with many such transferases demonstrating optimal efficiency when adding poly(A) sequence. For polyadenyltransferase mediated additions, the added sequence will generally be in the range of 5 to 50 nucleotides, preferably in the range of 6 to 25 nucleotides, more preferably in the range of 7 to 15 nucleotides.

In a preferred embodiment, the RNA polymerase promoter sequence is a T7 RNA polymerase promoter sequence comprising at least nucleotides −17 to +6 of a wild-type T7 RNA polymerase promoter sequence, preferably joined to at least 20, preferably at least 30 nucleotides of upstream flanking sequence, particularly upstream T7 RNA polymerase promoter flanking sequence. Additional downstream flanking sequence, particularly downstream T7 RNA polymerase promoter flanking sequence, e.g. nucleotides +7 to +10, may also be advantageously used. For example, in one particular embodiment, the promoter comprises nucleotides −50 to +10 of a natural class III T7 RNA polymerase promoter sequence. Table 1 provides exemplary promoter sequences and their relative transcriptional efficiencies in the subject methods (the recited promoter sequences are joined to a 23 nucleotide natural class III T7 promoter upstream flanking sequence).

TABLE I

Transcriptional efficiency of T7 RNA polymerase promoter sequences.

| Promoter Sequence | Transcriptional Efficiency |
|---|---|
| T AAT ACG ACT CAC TAT AGG GAG A (SEQ ID NO:1, class III T7 RNA polymerase promoter) | ++++ |
| T AAT ACG ACT CAC TAT AGG CGC (SEQ ID NO:2, Eberwine et al. (1992) supra) | + |
| T AAT ACG ACT CAC TAT AGG GCG A (SEQ ID NO:3, Bluescript, Stratagene, La Jolla, CA) | + |

The transcribed cDNA is initially single-stranded and may be isolated from the second RNA by any of a wide variety of established methods. For example, the method may involve treating the RNA with a nuclease such as RNase H, a denaturant such as heat or an alkali, etc., and/or separating the strands electrophoretically. The second strand cDNA synthesis may be effected by a number of well established techniques including 3'-terminal hairpin loop priming or methods wherein the polymerization is initiated at a noncovalently joined duplex region, generated for example, by adding exogenous primer complementary to the 3' end of the first cDNA strand or in the course of the Hoffman-Gubler protocol. In this latter embodiment, the cDNA isolation and conversion to double-stranded cDNA steps may be effected together, e.g. contacting the RNA with an RNase H and contacting the single-stranded cDNA with a DNA polymerase in a single incubation step. In any event, these methods can be used to construct cDNA libraries from very small, e.g. single cell, starting materials.

In a particular embodiment, the RNA transcription conditions employ a class III T7 promoter sequence (SEQ ID NO:1) and a T7 RNA polymerase under the following reaction conditions: 40 mM Tris pH 7.9, 6 mM $MgCl_2$, 2 mM Spermidine, 10 mM DTT, 2 mM NTP (Pharmacia), 40 units RNAsin (Promega), 300–1000 units T7 RNA Polymerase (6.16 Prep). The enzyme is stored in 20 mM HEPES pH 7.5, 100 mM NaCl, 1 mM EDTA, 1 mM DTT and 50% Glycerol at a protein concentration of 2.5 mg/mL and an activity of 300–350 units/uL. In exemplary demonstrations, 1–3 uL of this polymerase was used in 50 uL reactions. Starting concentrations of template can vary from picogram quantities (single cell level) to 1 ug or more of linear plasmid DNA. The final NaCl concentration is preferably not higher than 6 mM.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for normalizing and amplifying an RNA population comprising the steps of:
   copying message RNA (mRNA) to form first single-stranded (ss) cDNA;
   converting the first ss-cDNA to first double-stranded (ds) cDNA;
   linearly amplifying the first ds-cDNA to form first amplified RNA (aRNA);
   tagging the 3' end of the first aRNA with a known sequence to form 3'-tagged first aRNA;
   copying the 3'-tagged first aRNA to form second ss-cDNA; and
   normalizing the mRNA or the first aRNA.

2. A method according to claim 1, wherein the normalizing step comprises normalizing the mRNA.

3. A method according to claim 1, wherein the normalizing step comprises normalizing the first aRNA.

4. A method according to claim 1, wherein the normalizing step comprises normalizing both the mRNA and the first aRNA.

5. A method according to claim 1, further comprising the steps of:
   converting the second ss-cDNA to second ds-cDNA;
   linearly amplifying the second ds-cDNA to form second aRNA.

6. A method according to claim 1, further comprising the steps of:
   converting the second ss-cDNA to second ds-cDNA;
   linearly amplifying the second ds-cDNA to form second aRNA; and
   normalizing the second aRNA.

7. A method according to claim 1, further comprising the steps of:
   converting the second ss-cDNA to second ds-cDNA;
   linearly amplifying the second ds-cDNA to form second aRNA;
   normalizing the second aRNA;
   copying the second aRNA to form third ss-cDNA;
   converting the third ss-cDNA to third ds-cDNA; and
   linearly amplifying the third ds-cDNA to form third aRNA.

8. A method according to claim 1, wherein the tagging step comprises contacting the first aRNA with an oligonucleotide and a ligase, whereby the ligase adds the oligonucleotide to the 3' end of the first aRNA to form the 3'-tagged first aRNA.

9. A method according to claim 1, wherein the tagging step comprises contacting the first aRNA with a nucleotide and a polyadenyltransferase under conditions whereby the polyadenyltransferase adds the nucleotide to the 3' end of the first aRNA to form the 3' tagged first aRNA.

10. A method according to claim 1, wherein the converting step comprises:
    contacting the first ss-cDNA with RNase H and a DNA polymerase under conditions whereby the RNase H nicks the associated mRNA and the DNA polymerase initiates conversion at a noncovalently joined heteroduplex region and copies the first ss-cDNA to the first ds-cDNA.

11. A method according to claim 1, wherein the converting step comprises:
    contacting the first ss-cDNA with RNase H and a DNA polymerase under conditions whereby the RNase H nicks the associated mRNA and the DNA polymerase initiates conversion at a noncovalently joined heteroduplex region and copies the first ss-cDNA to the first ds-cDNA, wherein the polymerase provides 5' exonuclease activity.

12. A method according to claim 1, wherein the converting step comprises:
    contacting the first ss-cDNA with RNase H and a DNA polymerase under conditions whereby the RNase H nicks the associated mRNA and the DNA polymerase initiates conversion at a noncovalently joined heteroduplex region and copies the first ss-cDNA to the first ds-cDNA, wherein the polymerase lacks 5' exonuclease activity.

13. A method according to claim 1, wherein the mRNA copying step comprises:
    contacting the mRNA with a primer comprising an oligo dT sequence, an RNA polymerase promoter and an affinity tag.

14. A method according to claim 1, wherein the mRNA copying step comprises:
    contacting the mRNA with a primer comprising an oligo dT sequence, an RNA polymerase promoter and an affinity tag, wherein the affinity tag is biotin.

15. A method according to claim 1, wherein the mRNA copying step comprises:
    contacting the mRNA with a primer comprising an oligo dT sequence, an RNA polymerase promoter and an affinity tag, wherein the promoter activates an RNA polymerase selected from the group consisting of T7, T3 and SP6.

16. A method according to claim 1, wherein the amplifying step is effected with an RNA polymerase selected from the group consisting of T7, T3 and SP6.

17. A method according to claim 1, wherein the normalizing step comprises hybridizing the mRNA or the first aRNA with driver polynucleotides and then separating an unhybridized fraction of the mRNA or first aRNA.

18. A method according to claim 1, wherein the normalizing step comprises hybridizing the mRNA or the first aRNA with driver polynucleotides and then separating an unhybridized fraction of the mRNA or first aRNA, wherein the separating step is effected by a method selected from the group consisting of hydroxyapatite-based affinity separation and biotin-streptavidin-based affinity separation.

19. A kit for normalizing and amplifying an RNA population, said kit comprising instructions describing the method of claim 1 and a premeasured portions of oligo dT T7 biotinylated primer, T7 RNA polymerase, annealed biotinylated primers, streptavidin beads, polyadenyl transferase, reverse transcriptase, Rnase H, DNA pol I, buffers and nucleotides.

* * * * *